Figure 1:
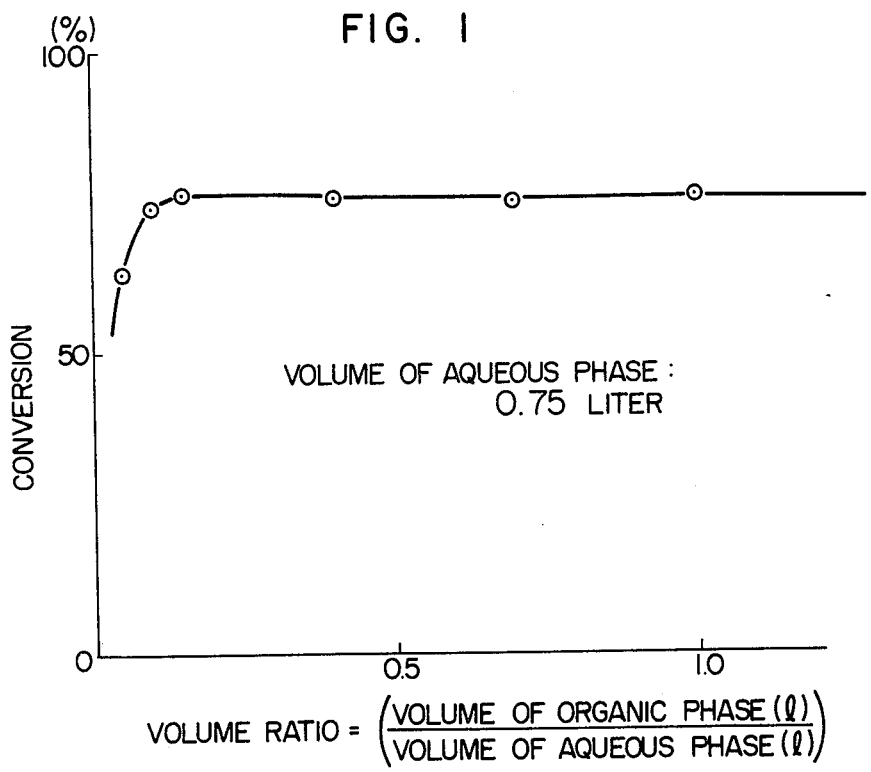

United States Patent [19]

Katoh et al.

[11] Patent Number: 4,474,981

[45] Date of Patent: Oct. 2, 1984

[54] PROCESS FOR PREPARING AN ACRYLIC OR METHACRYLIC ACID ESTER

[75] Inventors: Michio Katoh; Tadashi Abe, both of Niihama; Masanori Moriwaki, Ibaraki, all of Japan

[73] Assignee: Sumitomo Chemical Company, Limited, Osaka, Japan

[21] Appl. No.: 405,368

[22] Filed: Aug. 5, 1982

[30] Foreign Application Priority Data

Aug. 11, 1981 [JP] Japan .................. 56-126440

[51] Int. Cl.³ .............................................. C07C 67/08
[52] U.S. Cl. .................................................... 560/205
[58] Field of Search ........................................ 560/205

[56] References Cited

U.S. PATENT DOCUMENTS 3,712,917 1/1973 Sato et al. ............................ 560/205
3,781,332 12/1973 Sato et al. ............................ 560/205
3,875,212 4/1975 Ohrui et al. .......................... 560/205
4,329,492 5/1982 Andoh et al. ........................ 560/205

FOREIGN PATENT DOCUMENTS 2015509A 9/1979 United Kingdom .

*Primary Examiner*—Natalie Trousof
*Assistant Examiner*—L. Hendriksen
*Attorney, Agent, or Firm*—Stevens, Davis, Miller & Mosher

[57] ABSTRACT

A process for preparing an acrylic or methacrylic acid ester comprising esterifying the acrylic or methacrylic acid with an alcohol in a water-insoluble and non-reactive organic solvent in the presence of an acid catalyst, the volume ratio of the organic solvent phase to an aqueous solution phase of the acid catalyst being as small as 0.1 to 1.0, whereby a reactor is allowed to be small-sized and a conversion of the esterification is kept high. The acrylic or methacrylic acid ester is useful as a starting material of an acrylic resin or acrylic resin coating, an adhesive or the like.

1 Claim, 2 Drawing Figures

PROCESS FOR PREPARING AN ACRYLIC OR METHACRYLIC ACID ESTER

The present invention relates to a process for esterifying acrylic acid or methacrylic acid [hereinafter the both are referred to as (meth)acrylic acid]. More particularly, the present invention relates to a process for esterifying (meth)acrylic acid in the presence of an acid catalyst in a liquid/liquid heterogeneous system in which there coexist a water-insoluble non-reactive organic solvent.

The (meth)acrylic acid ester is important as a starting material of an acrylic resin or acrylic resin coating, an adhesive or the like.

In preparing (meth)acrylic acid esters from aqueous (meth)acrylic acid solutions obtained by the gas-phase catalytic oxidation of olefins or unsaturated aldehydes having 3 to 4 carbon atoms, a method is well known in which (meth)acrylic acid is extracted and separated from the aqueous (meth)acrylic acid solutions by using an organic solvent, and esterified in the presence of an organic solvent so as to be favorable for the reaction equilibrium of esterification.

For example, Japanese Patent Publication No. 41413/1974 discloses a process in which methacrylic acid is extracted with methyl methacrylate or ethyl methacrylate containing xylene, ethylbenzene or a mixture thereof, and the resulting extract is esterified in the presence of an acid catalyst and an alcohol while forming two phases, i.e. an aqueous and organic phase, contacting both phases with each other and heating. Also, Japanese Patent Publication No. 3338/1981 discloses a process in which the esterification is carried out using a sulfuric acid catalyst in a liquid/liquid heterogeneous system in which there coexists an organic solvent. Both of these processes carry out the esterification efficiently by forming two phases, i.e. an aqueous and organic phases in the presence of an organic solvent whereby the resulting ester is extracted with the organic phase to make the reaction equilibrium favorable. In these processes, however, it results that large quantities of organic solvent essentially independent of the esterification coexist in the reactor. It is therefore necessary to increase the volume of reactor according to the volume of organic solvent used, which leads to a reduction in the effect obtained by the foregoing efficient esterification.

As a process for avoiding this disadvantage, a process is conceived in which the amount of organic solvent supplied is decreased relatively to (meth)acrylic acid. In other words, the concentration of (meth)acrylic acid is increased. Japanese patent application Kokai (Laid-open) No. 115318/1979 discloses a process in which methacrylic acid is extracted with a mixed extracting agent containing a methacrylic acid ester and separated from a greater part of the agent by distillation, and then the resulting mixture comprising methacrylic acid and the remaining agent is used as a starting material for the esterification. This process, however, does not result in a reduction of the volume of organic phase, because, although the amount of organic solvent (e.g. xylene) in the organic phase in a reactor decreases, the amount of methacrylic acid ester increases.

As a result of extensive study on the characteristics of the esterification of (meth)acrylic acid, the present inventors found that, as shown in FIG. 1, the conversion of the esterification is influenced only by the volume of aqueous phase in a reactor, and that the efficiency of the conversion is maintained even by a fair reduction in the volume of organic phase. The present invention was completed based on this finding.

FIG. 1 shows a relation between volume ratio and conversion in the methyl-esterification of methacrylic acid, and was obtained by plotting the results of Examples 1 to 5 and Comparative example 1, and its summary will be explained simply. The methyl-esterification of methacrylic acid was carried out using a sulfuric acid catalyst in the presence of xylene, and this diagram shows a change in the conversion of the esterification when the volume of aqueous phase in a reactor was kept constant while that of organic phase was progressively varied. The abscissa indicates the ratio of the volume of organic phase to that of aqueous phase, meaning that the volume of organic phase decreases as the value of the ratio approaches to zero. Hereupon, the abscissa is referred to as "volume ratio" for brevity, and the volume ratio is expressed by the following equation:

$$\text{Volume ratio} = \frac{\text{Volume of organic phase in reactor (l)}}{\text{Volume of aqueous phase in reactor (l)}}$$

As is apparent from FIG. 1, it can be seen that the conversion of the esterification shows an approximately definite value in the region of the volume ratio of not less than 0.1, and the esterification proceeds independently of the volume of organic phase. In general, conversion lowers as reaction time (average residence time in vessel-type reactors) becomes shorter, but contrary to this, the result of FIG. 1 shows that the conversion is definite irrespective of the average residence time becoming shorter as the volume ratio decreases. The result of FIG. 1 may be explained as follows: When the esterification is carried out by forming two liquid phases like this patent application, most of the esterification proceeds in the aqueous phase because almost all the acid catalyst is present in the aqueous phase, and therefore the conversion is determined by the residence time of material in the aqueous phase.

As described above, even when the volume of organic phase in a reactor is reduced to a degree not lowering the effect of extracting the formed ester, the effect of the esterification does not lower; and a reduction of the volume of organic phase means a reduction of the size of reactor and besides, a reduction in stirring power, etc., and therefore many advantages can be expected. However, unlimited reduction of the volume ratio is not favorable for the following reasons.

Firstly, as shown in FIG. 1, a reduction of the conversion appears when the volume ratio approaches to a border line of approximately 0.1. This phenomenon may be considered to be that the effect of extracting the formed ester lowers according to an extreme reduction of the volume of organic phase, and as a result, that the concentration of the ester present in the aqueous phase increases to effect a shift of the reaction equilibrium. And, with a reduction of the conversion, disadvantages such as reduction of the ester yield or increase in costs for the recovery of unreacted (meth)acrylic acid, are not avoidable.

Secondly, a reduction of the volume ratio leads to an increase of the flow amount of the acid catalyst-containing aqueous phase supplied to a reactor. That is to say, the flow amount of the organic phase flowing out of the reactor is constant if the conditions except the volume ratio are the same, and the volume ratio ought to be the same as the ratio of the flow amount of effluent organic phase to that of effluent aqueous phase, so that the flow amount of aqueous phase increases in inverse proportion to the volume ratio. Consequently, the discard of the effluent aqueous phase as it is leads to a great increase in the amount of acid catalyst consumed and in a cost required for making said aqueous phase harmless. Also, as disclosed, for example, in Japanese Patent Publication No. 3338/1981, in a method in which the acid catalyst is to be used in circulation while maintaining its concentration in the aqueous phase constant by distilling water formed by the esterification out of the reactor, the circulation amount becomes tremendously large so that disadvantages such as increase in power cost and increase in the capacity of decanter for separation of effluent organic and aqueous phases, etc., are not avoidable.

As described above, the capacity of the esterification reactor can be made small by reducing the volume ratio, and the volume ratio is preferably 0.1 to 1.0, more preferably about 0.15 to about 0.5. On the other hand, an increase of the volume ratio is not desirable, as described hereinbefore, because it means the presence of organic solvent of larger amounts than required in the reaction system which is uneconomical, in other words, an increase in the capacity of the reactor. The result of FIG. 1 was obtained when the volume of aqueous phase was 0.75 liter. When the volume ratio is 1, the liquor volume in the reactor is 1.5 liters, while when the volume ratio is 2, the liquor volume clearly amounts to 2.25 liters, thus resulting really in a 50% increase in the capacity of the reactor, nevertheless without improvement in the conversion of the esterification. It is therefore advantageous to make the volume ratio not more than 1, and a further reduction to not more than 0.5 can enhance the effect to a larger extent.

As the organic solvent used in the present invention, those which are insoluble in water and inactive to the esterification are selected. But solvents having a boiling point which differ more largely from that of the formed ester are more preferred, and for example, xylene, ethylbenzene, cumene, cymene and mixtures thereof are preferred.

The present invention can be applied independently of the esterification temperature, but at temperatures less than 70° C., the reaction does not proceed sufficiently, while at those more than 100° C., a loss of (meth)acrylic acid caused by polymerization becomes significant. Consequently, the present invention can effectively be carried out at a reaction temperature of from 70° C. to 100° C., preferably from 75° C. to 95° C.

Figure 2:
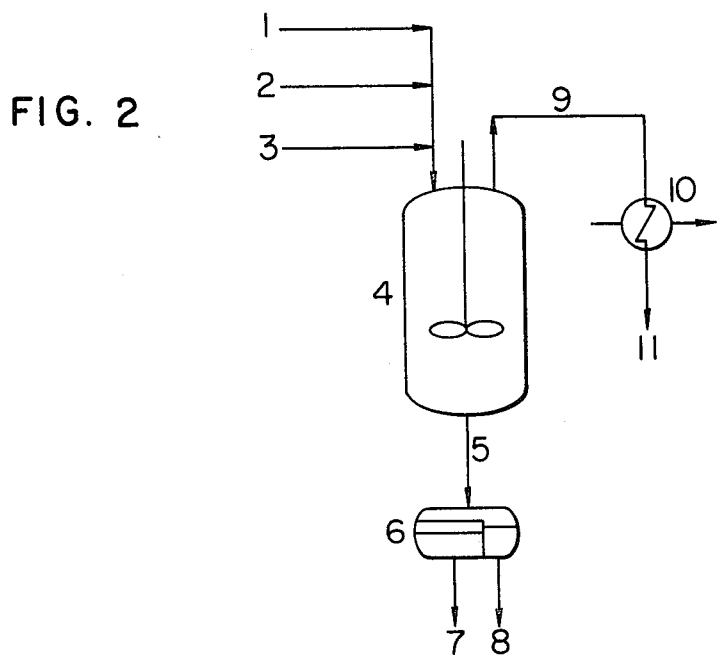

Next, the present invention will be illustrated in more detail with reference to FIG. 2. FIG. 2 shows one example of a flow sheet for one embodiment of the present invention, and is not to be interpreted as limiting the present invention to it alone. In the FIG. 2, 1, 2, 3, 5, 7, 8, 9 and 11 are lines, 4 is a reactor, 6 is a decanter and 10 is a condenser.

A mixture of (meth)acrylic acid as a starting material and a water-insoluble non-reactive organic solvent is supplied to a reactor 4 through the line 1, an alcohol as a starting material is supplied thereto through the line 2 and an acid catalyst is supplied through the line 3. The line 5 is a line of an effluent reaction liquor comprising an aqueous phase and an organic phase. The reaction liquor is separated into the aqueous and organic phases in a decanter 6, and the separated phases flow out of the decanter through lines 7 and 8, respectively. Through the line 9, water formed by esterification flows out of the reactor by azeotropic distillation together with a part of the organic solvent or formed ester, and after being condensed by a condenser 10, is sent to the next step through the line 11. It is desirable to regulate the amount of water passing through the line 9 so that the concentration of the acid catalyst in the aqueous phase has a pre-determined value within 10–30%. The acid catalyst supplied through the line 3 needs to be adjusted to a pre-determined concentration, and it is desirable that the aqueous phase having a definite acid catalyst concentration flowing out through the line 7, after being freed from polymers and the like by filtration, is circulated to the reactor 4 through the line 3, and that a fresh acid catalyst is supplied through the line 3 to make up for a loss of acid catalyst.

As another method for carrying out the present invention, the whole amount of the reaction liquor may be streamed through the line 5 without setting up the lines 9 and 11 and the condenser 10. In this case, since the aqueous phase flowing out through the line 7 contains water formed by reaction, it has a lowered concentration of acid catalyst. Consequently, it is a matter of course that the whole amount of the effluent aqueous phase can not be circulated, as it is, through the line 3, and that the formed water needs to be removed separately. In either of the embodiments, it is apparent that the volume ratio becomes equal to the ratio of the flow amount of organic phase flowing out through the line 8 to that of aqueous phase flowing out through the line 7. Since the flow amount of organic phase becomes definite under the same condition, the volume ratio can be decreased by increasing the flow amount of aqueous phase.

FIG. 2 shows a process of esterification using a single vessel, and needless to say, the present invention is not limited to this method, but can also be carried out with the same effect by the use of a multi-stage reaction vessel for not less than two stages.

Next, the method of the present invention will be illustrated in more detail with reference to the following examples.

EXAMPLE 1

Methacrylic acid was methyl-esterified using a 2-liter glass flask according to the flow sheet of FIG. 2 except that the whole amount of the aqueous phase flowing out through a line 7 was circulated through the line 3. The reaction system was operated under the following conditions: The flow rate of a supplied xylene solution containing 50 wt% of methacrylic acid, 500 ml/Hr; flow rate of methanol supplied, 250 ml/Hr; volume of the aqueous phase in the flask, 0.75 liter; volume of the organic phase in the flask, 0.3 liter (that is, volume ratio, 0.4). As a result, the sulfuric acid concentration of the aqueous phase could be kept at 20 wt% at a temperature of 83° C., and the conversion of methacrylic acid at that time was 75.5%.

EXAMPLES 2 TO 5, COMPARATIVE EXAMPLE 1

Operation was carried out in the completely same manner as in Example 1 except that the volume ratio in the flask was varied. Thus, results as shown in Table 1 were obtained.

TABLE 1

|  | Volume ratio | Volume of aqueous phase (liter) | Concentration of sulfuric acid (wt %) | Temperature (°C.) | Conversion (%) |
| --- | --- | --- | --- | --- | --- |
| Example 2 | 0.15 | 0.75 | 20 | 83 | 76.3 |
| Example 3 | 0.10 | 0.75 | 20 | 83 | 74.0 |
| Example 4 | 1.00 | 0.75 | 20 | 83 | 76.0 |
| Example 5 | 0.70 | 0.75 | 20 | 83 | 75.0 |
| Comparative example 1 | 0.05 | 0.75 | 20 | 83 | 63.0 |

EXAMPLE 6

Operation was carried out in the same manner as in Example 1 except that a xylene solution containing 70 wt% of acrylic acid and methanol were supplied at rates of 500 ml/Hr and 350 ml/Hr, respectively, and that the volume ratio was 0.15. As a result, the sulfuric acid concentration showed a definite value of 30 wt% at a reaction temperature of 80° C., and the conversion of acrylic acid at that time was 89%.

EXAMPLE 7

Operation was carried out in the same manner as in Example 6 except that 500 ml/Hr of ethanol was supplied as a starting material. As a result, the sulfuric acid concentration could be kept at 30 wt% at a reaction temperature of 85° C., and the conversion of acrylic acid at that time was 85.5%.

EXAMPLE 8

Operation was carried out in the same manner as in Example 1 except that a material comprising 50 wt% of methacrylic acid, 25 wt% of xylene and 25 wt% of ethylbenzene was supplied at a rate of 500 ml/Hr. As a result, the sulfuric acid concentration was kept at 20 wt% at a reaction temperature of 83° C., and the conversion of methacrylic acid was 76.0%.

What is claimed is:

1. A process for preparing an acrylic or methacrylic acid ester comprising esterifying the acrylic or methacrylic acid with an alcohol in a water-insoluble and non-reactive organic solvent in the presence of an acid catalyst, the volume ratio of the organic solvent phase to an aqueous solution phase of the acid catalyst being 0.15 to 0.5

* * * * *